United States Patent
Fujiwara et al.

(10) Patent No.: US 9,201,094 B2
(45) Date of Patent: Dec. 1, 2015

(54) WAFER EXAMINATION DEVICE AND WAFER EXAMINATION METHOD

(71) Applicants: Hirokazu Fujiwara, Miyoshi (JP); Narumasa Soejima, Seto (JP)

(72) Inventors: Hirokazu Fujiwara, Miyoshi (JP); Narumasa Soejima, Seto (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 79 days.

(21) Appl. No.: 14/100,737

(22) Filed: Dec. 9, 2013

(65) Prior Publication Data

US 2014/0159705 A1  Jun. 12, 2014

(30) Foreign Application Priority Data

Dec. 10, 2012  (JP) .................. 2012-269128

(51) Int. Cl.
| | |
|---|---|
| G01R 1/06 | (2006.01) |
| G01R 31/20 | (2006.01) |
| G01R 1/067 | (2006.01) |
| G01R 31/00 | (2006.01) |
| G01R 31/02 | (2006.01) |
| G01R 31/26 | (2014.01) |
| H01L 21/66 | (2006.01) |
| H01L 21/44 | (2006.01) |
| G01N 27/20 | (2006.01) |
| G01R 31/28 | (2006.01) |
| G01R 1/04 | (2006.01) |

(52) U.S. Cl.
CPC ............ *G01R 1/06755* (2013.01); *G01N 27/20* (2013.01); *G01R 1/0491* (2013.01); *G01R 1/067* (2013.01); *G01R 31/00* (2013.01); *G01R 31/2648* (2013.01); *G01R 31/2831* (2013.01); *G01R 31/2886* (2013.01); *H01L 22/00* (2013.01)

(58) Field of Classification Search
CPC .... G01R 1/067; G01R 31/00; G01R 31/2886; G01R 1/0491; G01R 31/2831; H01L 22/00
USPC .............. 324/149, 754.01, 755.01, 757.03, 324/762.05; 438/17–18, 661
See application file for complete search history.

(56) References Cited

U.S. PATENT DOCUMENTS

| | | | | |
|---|---|---|---|---|
| 3,641,402 | A * | 2/1972 | Revitz et al. | 257/750 |
| 4,764,026 | A * | 8/1988 | Powell et al. | 374/178 |
| 4,957,777 | A * | 9/1990 | Ilderem et al. | 438/677 |
| 6,054,868 | A * | 4/2000 | Borden et al. | 324/754.23 |
| 6,091,257 | A * | 7/2000 | Verkuil et al. | 324/754.1 |
| 6,198,300 | B1 * | 3/2001 | Doezema et al. | 324/755.07 |
| 2003/0164946 | A1 * | 9/2003 | Borden et al. | 356/432 |
| 2005/0095356 | A1 * | 5/2005 | Nakamura et al. | 427/58 |
| 2006/0076503 | A1 * | 4/2006 | Tsao | 250/396 R |
| 2008/0311736 | A1 * | 12/2008 | Mayer et al. | 438/602 |
| 2009/0001486 | A1 * | 1/2009 | Heck et al. | 257/415 |
| 2009/0020829 | A1 * | 1/2009 | Chandra et al. | 257/384 |
| 2012/0242356 | A1 * | 9/2012 | Ohuchi et al. | 324/705 |

FOREIGN PATENT DOCUMENTS

| | | |
|---|---|---|
| JP | 2011-138899 A | 7/2011 |
| JP | 2012-069567 A | 4/2012 |

* cited by examiner

*Primary Examiner* — Patrick Assouad
*Assistant Examiner* — Hoang X Nguyen
(74) *Attorney, Agent, or Firm* — Dinsmore & Shohl LLP

(57) ABSTRACT

A wafer examination device includes a probe, a fusion section and a measurement section. The probe is made of a metal which reacts with silicon carbide to produce silicide. The fusion section fuses the probe to a silicon carbide wafer as an examined object. The measurement section measures an electrical property of the silicon carbide wafer through the fused probe.

11 Claims, 3 Drawing Sheets

WAFER EXAMINATION DEVICE AND WAFER EXAMINATION METHOD

INCORPORATION BY REFERENCE

The disclosure of Japanese Patent Application No. 2012-269128 filed on Dec. 10, 2012 including the specification, drawings and abstract is incorporated herein by reference in its entirety.

BACKGROUND OF THE INVENTION

1. Field of the Invention

The present invention relates to a method for examining an electrical property of a silicon carbide wafer (also referred to as "SiC wafer" or "silicon carbide semiconductor wafer") and a device for the same.

2. Description of Related Art

In a manufacturing line for forming a semiconductor element on a silicon wafer, the electrical property of the silicon wafer is measured in order to maintain uniform quality. More specifically, an epitaxial layer (epilayer) is grown on the silicon wafer, and the electrical property of the epilayer is measured. The electrical property is typically the resistivity of the epilayer or the resistance value in a predetermined distance in the epilayer.

A four-point probe method has been known as a method for measuring the electrical property of a wafer. This method is performed as follows. Four probes are first brought into contact with a silicon wafer on which the epilayer is grown at prescribed intervals in a straight line. Current is then applied to the two outer probes, and the voltage between the two inner probes is measured. Given that the flowing current is I, the measured voltage is V, and the distance between the probes is L, resistivity R can be obtained by an equation, $R=2\pi LV/I$. Such a method is disclosed in Japanese Patent Application Publication No. 2011-138899 (JP 2011-138899 A).

As another method for measuring the electrical property of a wafer, a method has been known in which a small electrode pad dedicated to measurement is formed on a wafer. Such an electrode pad for measurement is referred to as "Test Element Group (TEG)" (Japanese Patent Application Publication No. 2012-069567 (JP 2012-069567 A)).

The four-point probe method of the related art may not be able to accurately measure the electrical property depending on a kind of the silicon wafer (or properties of a layer formed in a wafer shape). A typical case of such is where the resistivity between the probes and the wafer depends on the magnitude or direction of the applied current or voltage. Independence of the resistivity from the magnitude or direction of the applied current or voltage is referred to as "ohmic characteristic". In other words, a linear relationship between current and voltage (Ohm's law) substantially holds in the ohmic characteristic. The resistance value between two materials (the probes and the wafer) may become more or less non-linear according to the voltage and the current; however, contact that allows a substantial linear relationship to hold is referred to as "ohmic contact". Because the sufficient ohmic characteristic cannot be secured between the probes and the wafer depending on a kind of the silicon wafer, the electrical property of the epilayer may not be accurately measured.

One of the wafers in which the ohmic characteristic cannot be secured only by bringing the probes into contact is a silicon carbide wafer (also referred to as "SiC wafer" or "silicon carbide semiconductor wafer"). The silicon carbide wafer has recently been used for a power element. As exemplified in JP 2012-069567 A, it is considered to form a TEG on the wafer and thereby measure the electrical property in order to measure the electrical property of the silicon carbide wafer. However, formation of the TEG requires large cost.

SUMMARY OF THE INVENTION

The present invention provides a technique that improves a four-point probe method and enables measurement of a silicon carbide wafer by the four-point probe method.

A first aspect of the present invention provides a wafer examination device including: a probe made of a metal which reacts with silicon carbide to produce silicide; a fusion section which fuses the probe to a silicon carbide wafer as an examined object; and a measurement section which measures an electrical property of the silicon carbide wafer through the fused probe.

The probe may include a core of silicon carbide and a coating material which contains the metal and is coated on the core. Further, the metal may include at least one of nickel, titanium, aluminum, chromium, tantalum, molybdenum, tungsten, and cobalt. For example, when the probe of silicon carbide that is coated with nickel is fused to the silicon carbide wafer, nickel diffuses in the silicon carbide wafer, and a nickel silicide alloy ($Ni_2Si$) is formed on an interface between the probe and the silicon carbide wafer. The conductivity between the probe and the silicon carbide wafer is improved by the nickel silicide alloy as a medium, thereby securing an ohmic characteristic.

The fusion section that fuses the probe may be an energizing device that applies current to the silicon carbide wafer through the probe. Further, the fusion section may be configured to apply higher current to the probe than current which is applied to the probe when the electrical property is measured by the measurement section. Alternatively, the fusion section may be configured to apply an electric pulse to the probe at a higher voltage than a voltage at which an electric pulse is applied to the probe when the electrical property is measured by the measurement section. The probe generates heat by the high current or the high voltage pulse, and the metal (for example, nickel) coated on the core is melted to fuse the probe to the silicon carbide wafer.

A second aspect of the present invention provides a wafer examination method. The wafer examination method includes a fusion step and an examination step. In the fusion step, a probe made of a metal which reacts with silicon carbide to produce silicide is fused to a silicon carbide wafer as an examined object. In the examination step, an electrical property of the silicon carbide wafer is measured through the fused probe.

The electrical property of the single silicon carbide wafer is measured for plural times, an average of measurement results is obtained, and the electrical property may thereby highly accurately be identified. However, the above-described wafer examination method fuses the probe to a surface of the silicon carbide wafer. Accordingly, the above-described wafer examination device may further include a removal step of removing the fused probe and a fused mark of the probe from the silicon carbide wafer. After the removal step, the fusion step and the examination step may be performed again on the silicon carbide wafer whose electrical property has been measured. The above-described wafer examination method includes the removal step, and the measurement can thereby be performed on the single silicon carbide wafer for plural times. Ion addition and an activation annealing treatment may be performed for the epilayer prior to every measurement.

BRIEF DESCRIPTION OF THE DRAWINGS

Features, advantages, and technical and industrial significance of exemplary embodiments of the invention will be described below with reference to the accompanying drawings, in which like numerals denote like elements, and wherein.

DETAILED DESCRIPTION OF EMBODIMENTS

In an embodiment of the present invention, probes are not simply brought into contact, but special probes are used and fused to a silicon carbide wafer. Conductivity between the probes and the silicon carbide wafer is improved by the fusion, thereby securing an ohmic characteristic. Specifically, probes that can produce a silicide alloy on an interface with the silicon carbide wafer are used to fuse the probes to the silicon carbide wafer. Because the silicide alloy is stable and has high electric conductivity, the ohmic characteristic between the probes and the silicon carbide wafer is improved.

In the embodiment of the present invention, a silicon carbide wafer on which an epitaxial layer is grown on a surface layer of a substrate is prepared prior to a fusion step. The epitaxial layer is grown by adding a P-type (N-type) dopant to a surface layer of a P-type (N-type) substrate. It should be noted that the substrate may be either one of P-type and N-type and the grown epitaxial layer can be either one of P-type and N-type.

Figure 1:
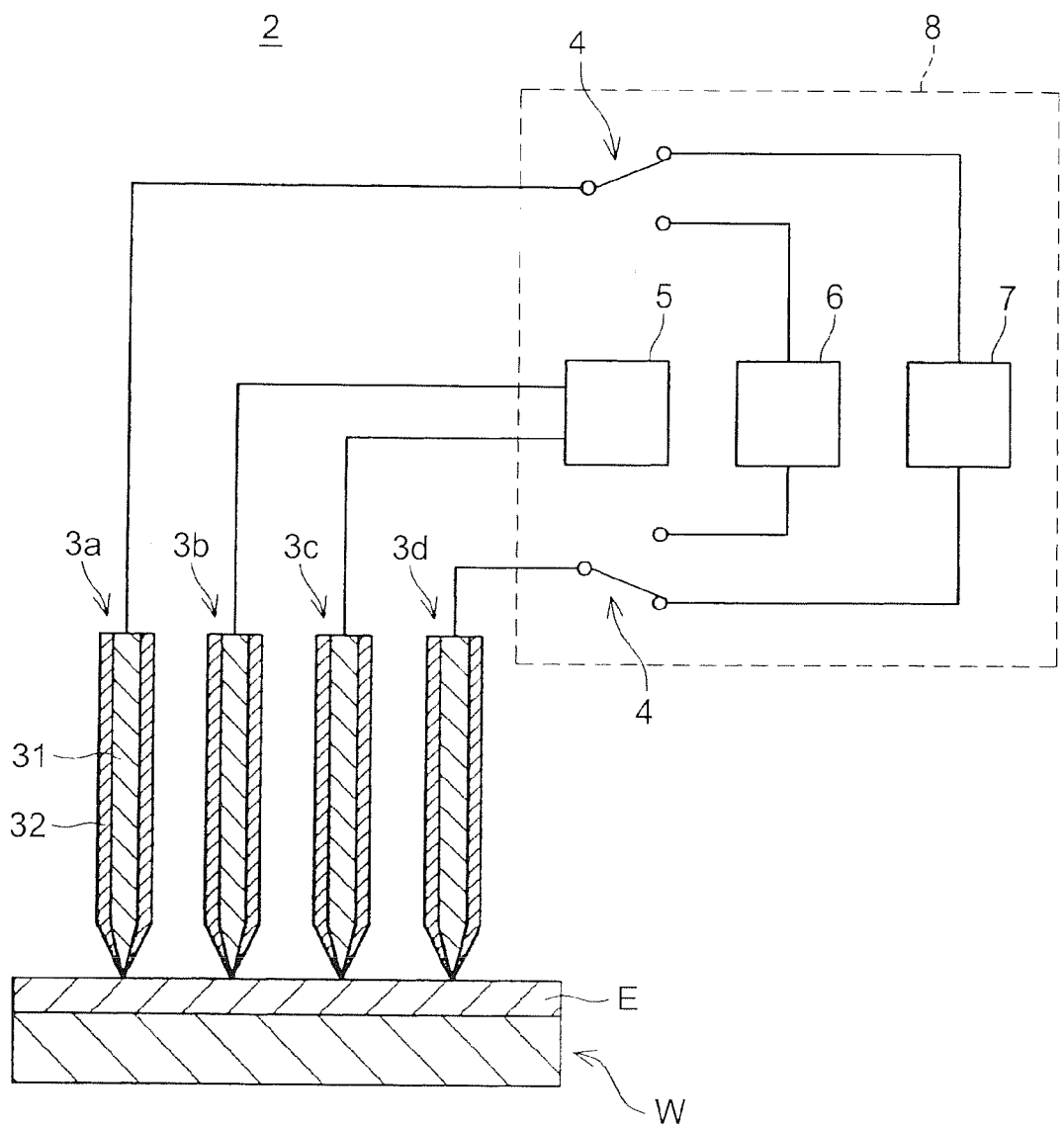
FIG. 1 is a schematic view of an examination device of a silicon carbide wafer of the embodiment of the present invention.

A wafer examination device of the embodiment will be described with reference to drawings. The wafer examination device will hereinafter be simply referred to as "examination device". Further, the silicon carbide wafer will simply be referred to as "wafer". FIG. 1 shows a schematic view of an examination device 2. A wafer W denotes the wafer (silicon carbide wafer) as an examined object.

The examination device 2 is a device for measuring resistance (sheet resistance) of a surface layer of the wafer W. An N-type epitaxial layer (epilayer E) has previously been grown on a surface layer of the wafer W (P-type) as the examined object.

The examination device 2 includes four probes 3a, 3b, 3c, 3d, and a measurement device 8. Hereinafter, when any one of the four probes is represented, it will be denoted as "probe 3". The four probes have the same structures. In the probe 3, a nickel coat 32 is provided on a surface layer of a core 31 made of silicon carbide. The four probes are linearly fixed to a holder (not shown) at regular intervals. The holder vertically slides. After the wafer W is set, the holder moves down the four probes 3 such that tips of the probes 3 contact the surface layer of the wafer W as in FIG. 1. Here, as shown in the figure, the two outer probes correspond to the probes 3a, 3d, and the two inner probes correspond to the probes 3b, 3c.

The measurement device 8 includes a voltmeter 5, a constant current output unit 6, a voltage pulse generator 7, and a selector 4. The voltmeter 5 is connected to the inner probes 3b, 3c. The outer probes 3a, 3d are connected to either one of the constant current output unit 6 and the voltage pulse generator 7 by the selector 4.

Usage of the examination device 2 will be outlined. The examination device 2 applies a prescribed value of current to the two outer probes 3a, 3d in a state where the four probes 3 are fused to the surface layer of the wafer W and then measures the voltage between the two inner probes 3b, 3c. Because the probes 3 are fused to the wafer W, the ohmic characteristic is secured between the probes 3 and the wafer W, and the sheet resistance can thus accurately be measured. Further, after the sheet resistance is once measured, the fused probes are removed from the wafer, and surface portions of the wafer in which nickel silicide is produced are also removed. The measurement of the sheet resistance is repeated by fusing the probes again. The same measurement positions (positions which the probes 3 contact) as a previous time are used. An average of measurement results from plural times is obtained, and further accurate sheet resistance can thereby be obtained. A method of measuring the sheet resistance at each time is basically the same as a conventional four-point probe method except that the probes 3 are fused.

Figure 2:
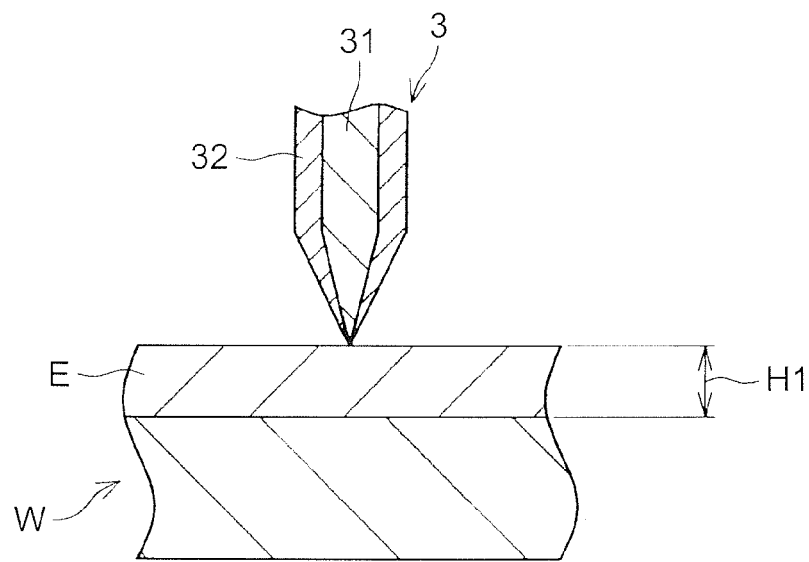
FIG. 2 explains an examination method of the embodiment of the present invention (probe application step)
Figure 3:
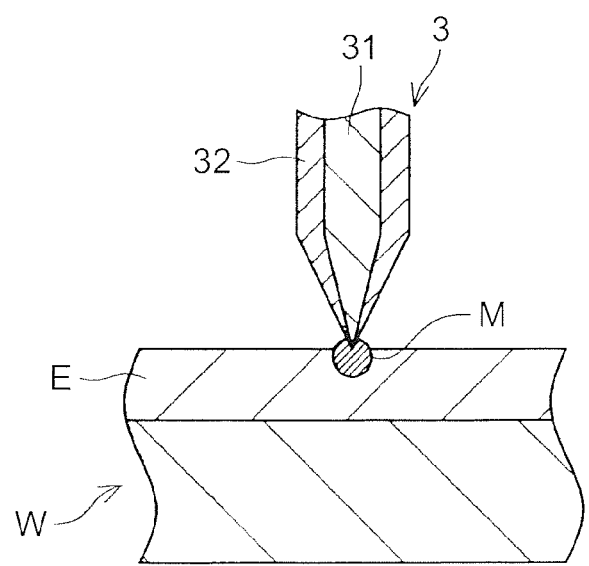
FIG. 3 explains the examination method of the embodiment of the present invention (fusion step)
Figure 4:
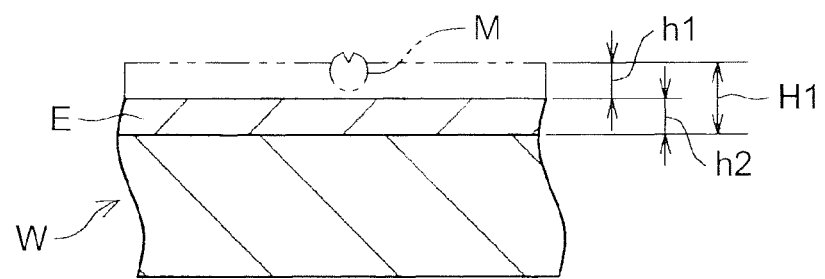
FIG. 4 explains the examination method of the embodiment of the present invention (removal step)
Figure 5:
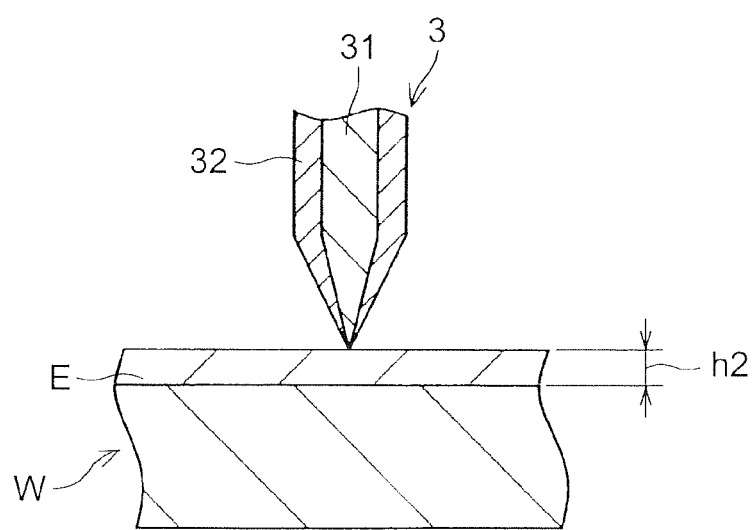
FIG. 5 explains the examination method of the embodiment of the present invention (second probe application step).

An examination method will be described in detail with reference to FIGS. 2 to 4. Although FIGS. 2 to 4 show one of the four probes for description, the other probes are the same.

Before the description of the examination, preparation of the wafer W as the examined object will be described. The N-type epitaxial layer (epilayer E) is first produced on the surface layer of the P-type wafer W (silicon carbide wafer). The epilayer E is grown by doping nitrogen in the surface layer of the wafer W, for example. A thickness of the epilayer of approximately one micrometer allows measurement of the sheet resistance. However, because measurement is again performed after the surface layer is removed as described above, the epilayer E is grown to approximately 5 micrometers to 20 micrometers. A thickness of five micrometers allows repeated measurement of the sheet resistance for about five times, and a thickness of 20 micrometers allows repeated measurement for about 20 times.

Further, prior to the measurement, presence or absence of crystal defect in the epilayer E is examined, and positions where no crystal defect is present are determined as measurement positions of the sheet resistance (that is, positions which the probes 3 contact). An existing technique such as a photoluminescence method may be used for a search for crystal defects. The photoluminescence method can identify positions of stacking faults and threading dislocations that are present in the epilayer E.

Ions are next added to the epilayer E, and activation annealing is performed. An example of a condition of the ion addition is P-type, aluminum ion, $1.0 \times 19 \, cm^3$, 420 KeV, a depth of 0.4 micrometers. Further, an example of an annealing condition is 1700° C. in an argon atmosphere and 30 minutes.

The wafer W prepared as described above is set in the examination device 2, and the measurement of the sheet resistance is started. The tips of the four probes 3 are first brought into contact with previously specified measurement positions on the surface of the wafer W (probe application step, see FIG. 2). A thickness H1 denotes the thickness (depth) of the epilayer E.

The two outer probes 3a, 3d are next connected to the voltage pulse generator 7, and a high voltage pulse is applied between the probes 3a, 3d. Application of the high voltage pulse causes electric discharge at the tips of the probe 3, and the temperature of the probes 3 increases. The examination device 2 applies the voltage pulse to an extent that the temperature of the tips of the probes 3 exceeds 890° C. that is the melting point of nickel. When nickel in the tips of the probes melts, the melted nickel diffuses in the epilayer and produces a nickel silicide alloy, and the tips of the probes 3 fuse to the wafer W (fusion step, see FIG. 3). An area M in FIG. 3 represents an area containing the nickel silicide alloy. Both of depth and width of the area M are actually in 0.1 micrometer order. FIG. 3 shows the area M in a larger size for easier understanding. When the voltage pulse is applied to the two outer probes 3a, 3d, pulse current flows between the two inner probes 3b, 3c, and all the probes fuse.

In a state of FIG. 3, nickel coated on the probes 3 serves as a fusion material to form the nickel silicide alloy ($Ni_2Si$) on interfaces between the probes 3 and the wafer W, and the probes 3 fuse to the wafer W. The work function of nickel is 5.2 eV, and the work function of nickel silicide is 4.8 eV. Therefore, the barrier height between the probes 3 and the wafer W lowers, thereby improving the ohmic characteristic. Further, nickel coated on the probes 3 diffuses in the epilayer E of silicon carbide to form nickel silicide with high crystallinity, thereby securing a higher ohmic characteristic.

After the ohmic characteristic is improved by fusing the probes 3 to the wafer W, the four probes 3 are used to measure the sheet resistance of the epilayer E (measurement step). The selector 4 is operated to switch the connection of the outer probes 3a, 3d from the voltage pulse generator 7 to the constant current output unit 6. While constant current is applied between the outer probes 3a, 3d, the voltage between the inner probes 3b, 3c is measured by the voltmeter 5. A value measured by the voltmeter 5 is used to obtain the sheet resistance. The measurement method described herein is the same as a conventional four-point probe method except that the probes 3 are fused to the wafer W, and a detailed description will thus be omitted. As described above, a first measurement of the sheet resistance is finished.

The fused probes 3 are next removed, and the surface of the wafer W is polished to remove fused marks (removal step, see FIG. 4). Here, the fused mark of the probe is an area of the nickel silicide alloy that is formed on the surface layer of the epilayer E. A method such as chemical mechanical polishing is used to remove the fused marks. For example, if the thickness H1 of the first epilayer is two micrometers and nickel silicide is produced in the surface layer within one micrometer from the surface when the probes 3 are fused, the one micrometer surface is removed, and the new epilayer E in a thickness of one micrometer can thereby be obtained on the surface of the wafer W. In FIG. 4, a thickness h1 denotes the thickness of the epilayer E to be removed, and a thickness h2 denotes the thickness of the remaining epilayer E. In this example, the initial thickness of the epilayer, H1=2 micrometers; the thickness of the epilayer to be removed, h1=1 micrometer; and the thickness of the remaining epilayer, h2=1 micrometer.

Next, the ion addition and activation annealing is again performed for the remaining epilayer E. The probes 3 are then brought into contact with the epilayer E, and the above-described probe application step, fusion step, and measurement step are repeated. Positions which the probes 3 again contact are the same as a previous time. The positions same as the previous time mean the specified positions where no crystal defect is present when crystal defects are searched for the first time.

As described above, the probes 3 are brought into contact with the same positions and fused thereto to again measure the sheet resistance. The same treatment is repeated, and the sheet resistance is measured in the same position for plural times. An average of the plurality of the measurement results of the sheet resistance is finally obtained and is output as the sheet resistance of the epilayer of the wafer W.

The above-described examination device and examination method measure the sheet resistance after the probes 3 are fused to the wafer W and the ohmic characteristic therebetween is thereby improved. Because the ohmic characteristic is improved, accurate sheet resistance can be obtained.

Points to be noted about the above-described technique will be described. The probes 3 of the embodiment are the cores 31 that are made of silicon carbide and coated with nickel. A coating material is not limited to nickel but may be metals that can produce silicide alloys with silicon carbide. Known examples of such metals other than nickel are titanium, aluminum, chromium, tantalum, molybdenum, tungsten, cobalt, and so forth. Further, it is sufficient that the coating material contains the above-described metals, and the coating material may contain another component such as a catalyst that facilitates production of a silicide alloy.

It is preferable that when the four probes are fused to the wafer, the inner probes 3b, 3c are removed from the voltmeter 5 and connected to negative electrodes of the voltage pulse generator. This is to protect the voltmeter 5 from the voltage pulse and facilitate fusion of the inner probes 3b, 3c.

The voltage pulse generator 7 of the embodiment may be regarded as an example of a fusion section. The measurement device 8 may be regarded as an example of a measurement section. The fusion section is not limited to the voltage pulse generator 7, but a device is sufficient that increases the temperature of the tips of the probes to the melting point of the coating material in a short time. The fusion section may be a device that can apply high current in a short time other than the voltage pulse generator. Further, the fusion section may be a device that vibrates the tips of the probes by a high-frequency wave and joins the tips to the surface of the wafer by friction (friction joining device). Moreover, a measurement device that applies current for measurement between the probes when the electrical property of the silicon carbide wafer is measured may be utilized as the fusion section. In other words, the measurement device may apply an electric pulse at a higher voltage than the measurement to the silicon carbide wafer. Utilization of the measurement device allows realization of the wafer examination device at a reasonable cost.

The thickness of the epilayer E can be determined according to a desired repetition frequency of the examination. For example, in a case where it is known that the silicide alloy reaches to a depth of one micrometer when the probes are fused and 20 times of measurement are desired on the single wafer, it is sufficient to grow the epilayer to a thickness of at least 20 micrometers.

The examination device of the embodiment adopts the four-point probe method; however, the technique disclosed by this specification is not limited to the four-point probe method. The technique disclosed by this specification may be applied to a device that brings two probes into contact with the silicon carbide wafer and measures the electrical property (electric resistance) of the wafer between the probes. The technique disclosed by this specification can also be applied to a device that brings the probes into contact with face and back surfaces of the silicon carbide wafer and measures the electric resistance between the face and back surfaces, for example.

The examination device 2 of the embodiment is a device for measuring the resistance (sheet resistance) of the surface layer of the wafer W. A measured subject of the sheet resistance may be an epilayer to which ion addition and an activation treatment are performed.

A measured object of the examination device 2 of the embodiment is the P-type wafer W (silicon carbide wafer) whose surface layer is produced with the N-type epitaxial layer (epilayer E). It should be noted that the technique disclosed by this specification is not limited by conductivity types of substrates as measured objects and epitaxial layers.

In the foregoing, specific examples of the present invention have been described in detail. However, those are only examples and do not specifically limit the present invention. The present invention includes the described specific examples that are variously modified and changed.

What is claimed is:

1. A wafer examination device, comprising:
a probe made of a metal which reacts with silicon carbide to produce silicide;
a fusion section which fuses the probe to a silicon carbide wafer as an examined object; and
a measurement section which measures an electrical property of the silicon carbide wafer through the fused probe.

2. The wafer examination device according to claim 1, wherein
the probe includes a core of silicon carbide and a coating material which contains the metal and is coated on the core, and
the metal includes at least one of nickel, titanium, aluminum, chromium, tantalum, molybdenum, tungsten, and cobalt.

3. The wafer examination device according to claim 1, wherein the fusion section is an energizing device which applies current to the silicon carbide wafer through the probe.

4. The wafer examination device according to claim 3, wherein the fusion section is configured to apply higher current to the probe than current which is applied to the probe when the electrical property is measured by the measurement section.

5. The wafer examination device according to claim 3, wherein the fusion section is configured to apply an electric pulse to the probe at a higher voltage than a voltage at which the electric pulse is applied to the probe when the electrical property is measured by the measurement section.

6. A wafer examination method, comprising:
a fusion step of fusing a probe made of a metal which reacts with silicon carbide to produce suicide to a silicon carbide wafer as an examined object; and
an examination step of measuring an electrical property of the silicon carbide wafer through the fused probe.

7. The wafer examination method according to claim 6, further comprising:
a removal step of removing the fused probe and fused mark of the probe from the silicon carbide wafer,
wherein after the removal step, the fusion step and the examination step are again performed on the silicon carbide wafer whose electrical property has been measured.

8. The wafer examination method according to claim 6, wherein the metal includes at least one of nickel, titanium, aluminum, chromium, tantalum, molybdenum, tungsten, and cobalt.

9. The wafer examination method according to claim 7, wherein when the fusion step and the examination step are again performed, a position on which the probe is contacted is a same position as the fusion step previously performed.

10. The wafer examination method according to claim 7, further comprising:
an epilayer production step of producing an epitaxial layer on a surface layer of the silicon carbide wafer, the epitaxial layer having a thickness from 5 micrometers to 20 micrometers,
wherein in the removal step, the fused mark of the probe is removed together with the surface layer of the silicon carbide wafer.

11. The wafer examination method according to claim 6, further comprising:
an examined position determination step of determining, by examining presence or absence of a crystal defect in an epitaxial layer of the silicon carbide wafer prior to a first examination of the silicon carbide wafer, a position where no crystal defect is present as a position on which the probe is contacted.

* * * * *